(12) United States Patent
Liversidge

(10) Patent No.: US 8,617,119 B2
(45) Date of Patent: Dec. 31, 2013

(54) MEDICAL NEEDLE SAFETY DEVICE

(75) Inventor: Barry Peter Liversidge, Colchester (GB)

(73) Assignee: Tip-Top.Com Ltd., Colchester, Essex (GB)

( * ) Notice: Subject to any disclaimer, the term of this patent is extended or adjusted under 35 U.S.C. 154(b) by 232 days.

(21) Appl. No.: 12/839,157

(22) Filed: Jul. 19, 2010

(65) Prior Publication Data

US 2010/0286623 A1 Nov. 11, 2010

Related U.S. Application Data

(63) Continuation of application No. 12/160,046, filed as application No. PCT/GB2007/050004 on Jan. 4, 2007, now abandoned.

(30) Foreign Application Priority Data

Jan. 6, 2006 (GB) .................................. 0600212.5

(51) Int. Cl.
*A61M 5/32* (2006.01)

(52) U.S. Cl.
USPC ........... 604/192; 604/198; 604/193; 604/194; 604/195; 604/187; 604/110

(58) Field of Classification Search
USPC ......... 604/198, 192, 193–195, 110, 187, 263, 604/246, 256
See application file for complete search history.

(56) References Cited

U.S. PATENT DOCUMENTS

| 4,966,592 A | 10/1990 | Burns et al. |
| 5,433,712 A | 7/1995 | Stiles et al. |
| 6,676,638 B2 | 1/2004 | Takagi et al. |
| 6,676,641 B2 | 1/2004 | Woodard et al. |

(Continued)

FOREIGN PATENT DOCUMENTS

| WO | WO 99/32177 | 7/1999 |
| WO | WO0176665 | 10/2001 |

(Continued)

OTHER PUBLICATIONS

International Search Report dated Apr. 11, 2007, PCT/GB2007/050004, pp. 1-3.

(Continued)

*Primary Examiner* — Kevin C Sirmons
*Assistant Examiner* — Edelmira Bosques
(74) *Attorney, Agent, or Firm* — Andrus, Sceales, Starke & Sawall, LLP

(57) ABSTRACT

A safety device having a tubular support for a needle mount end and a protective shield slidably mounted on the support from a set position, a retracted position and then to a locked position to covers the needle. A locking member mounted on the support, within the shield and a cam follower is engaged with a cam profile on the locking member. Forward axial movement of the support relative to the locking member causes the locking member to rotate relative to the support. The shield has a guide defining a shoulder towards its rearward end and an abutment on the locking member is receivable behind the shoulder when the shield is in its locked position. A spring acts such that when the locking member is turned to engage its abutment with the shoulder of the shield when the latter is in its locked position, so preventing subsequent rearward movement thereof.

19 Claims, 6 Drawing Sheets

(56) References Cited

U.S. PATENT DOCUMENTS

| | | |
|---|---|---|
| 6,846,302 B2 | 1/2005 | Shemesh et al. |
| 7,192,416 B1 | 3/2007 | Lazzaro et al. |
| 7,297,136 B2 | 11/2007 | Wyrick |
| 2001/0037088 A1 | 11/2001 | Domici et al. |
| 2004/0122375 A1* | 6/2004 | Woodard et al. ............... 604/218 |
| 2004/0230158 A1 | 11/2004 | Malenchek |
| 2006/0282044 A1 | 12/2006 | Mohammed |
| 2007/0129674 A1 | 6/2007 | Liversidge |
| 2007/0270759 A1 | 11/2007 | Pessin |

FOREIGN PATENT DOCUMENTS

| | | |
|---|---|---|
| WO | WO03045480 | 6/2003 |
| WO | WO03045481 | 6/2003 |
| WO | WO2005035030 | 4/2005 |

OTHER PUBLICATIONS

Oxford English Dictionary, 2nd Ed, 1989, bungee, pp. 1-4.

* cited by examiner

MEDICAL NEEDLE SAFETY DEVICE

CROSS REFERENCE TO RELATED APPLICATION

The present application is a continuation of U.S. patent application Ser. No. 12/160,046, filed Jul. 3, 2008, now abandoned, which in turn is the U.S. national stage application of International Application PCT/GB2007/050004, filed Jan. 4, 2007, which international application was published on Jul. 12, 2007 as International Publication WO 2007/077463. The International Application claims priority of British Patent Application 0600212.5, filed Jan. 6, 2006.

This invention relates to a safety device for a medical needle having a mount end and a sharp tip, intended for penetration of a human or animal body, or for other medical uses such as the penetration of a pierceable membrane of an intravenous medication system. The invention further relates to a safety device including a medical needle as aforesaid, ready for use. For convenience, in the following all such medical uses will be described simply as the penetration of a body, even though specific embodiments may be intended for other medical uses.

Throughout this specification the terms forward and forwardly used in relation to the safety device refer to the end thereof which is approached to a body when a procedure is to be performed, and the direction towards that end. Conversely, the terms rearward and rearwardly refer to the end of the safety device opposed to the forward end and the direction away from that forward end.

Fluids of various kinds may be administered to a human or animal body by means of a hollow needle in conjunction with a source of the required fluid. For example, such a needle may be used in conjunction with a syringe holding a liquid drug which may be contained directly in the syringe barrel or in a cartridge located within the syringe, the needle being used to penetrate the body at the site at which the drug is to be received. Equally, body fluids may be withdrawn by using a hollow needle which is used to penetrate the body until the tip is located at the site from which fluid is to be withdrawn.

A recognised hazard for clinicians and other persons using medical needles for the above described purposes, as well as people who may be exposed to used needles in the course of the disposal of those needles, is the risk of a so-called needle-stick injury—that is to say the accidental penetration of a person's skin by the needle. Prior to the use of the needle to supply a fluid to or to withdraw fluid from a body, this rarely presents much of a problem, though once the needle has been used on a body, there is a very much higher risk of a serious consequence for a person suffering a needle-stick injury. During use of the needle to penetrate the body tissues of a patient, the needle is likely to become contaminated with various organisms; should a person subsequently suffer a needle-stick injury, infection could occur.

There have been numerous proposals for protecting the sharp tip of a used needle, in order to reduce the risk of a needle-stick injury following use of the needle. Some proposals have actually increased the likelihood of such an injury by virtue of the action which must be performed to protect the tip, even if the risk thereafter is lessened. Despite all of the proposals which have previously been made, very few have achieved commercial success, nor has there been wide acceptance by the medical industry. Many proposals are somewhat complex and involve a significantly greater manufacturing cost, and so are unacceptable on economic grounds. Others are much more difficult to use as compared to an unprotected needle, and so are rejected by clinicians. Yet further proposals do not allow compliance with best practice protocols.

A device which protects a needle tip after use without an operator having to perform any extra step on withdrawing the needle from a body is usually referred to as a passive protection device. This may be contrasted with an active protection device, where an operator is required to perform an extra step in order to protect a needle, following the withdrawal of the needle from a body. The requirement to perform an extra step leaves the needle unprotected for a longer period than with a passive protection device and further the performance of that extra step exposes the operator to a potentially hazardous situation, when needle-stick accidents can occur.

There is a significant demand for a passive protection device for use with a needle, and which allows a clinician or perhaps others to use the needle in much the same way as is done with an unprotected needle, but which can be manufactured economically and which provides a high degree of protection against needle-stick injury. In the case of health professionals, this demand is driven by health and safety legislation but in the case of others performing self-injections using a so-called pen injector, the used needles must be disposed of safely with minimum risk to others, even in the event that a sharps container is not immediately available. Further, particularly for self-injections, it is highly preferred that the device operates fully automatically, without intervention by the user, so as wholly to prevent access to the needle tip after use, other than by a determined attempt to override the protection. In this way, protection may be afforded not just to the clinician or other user of the needle, but also to people who could come into a risky situation with used needles, such as waste disposal operators, cleaners, and so on.

Particularly in the case of a pen injector, it is advantageous for a passive protection device to have three positions: an initial or set position where the device is ready for use preferably with a portion of the needle from its tip exposed for performing the injection; an injecting position where the full length of the needle is exposed and fully penetrates the body; and a locked position where a shield wholly covers the needle and is locked against movement thereby preventing exposure of at least the needle tip.

The present invention aims at providing a safety device advantageously in the form of an accessory for an injector, which addresses these issues and which is both relatively simple and economic to manufacture, especially on a fully automated production line, and which does not significantly affect a conventional injection procedure when mounted on an injector.

According to this invention, there is provided a safety device for a medical needle having a mount end and a sharp tip, which device comprises:

a tubular support adapted for direct or indirect association with the needle mount end;
  a tubular protective shield disposed co-axially on the support for sliding movement with respect thereto from a set position where the shield covers a needle with which the support is associated to a retracted position where a part of the length of an associated needle back from its tip is exposed, and then to a locked position where the shield again covers the needle to afford protection thereto, the shield and support being restrained against significant relative rotational movement;
  a locking member rotationally mounted on the support within the shield, there being a cam profile on one of the locking member and support and a cam follower on the other of the locking member and support whereby forward axial movement of the support with respect to the locking member causes the locking member to rotate relative to the support;

a guide extending generally axially of the shield and defining a shoulder towards the rearward end thereof;

an abutment on the locking member engageable with the guide and receivable behind the shoulder when the shield is in its locked position;

a stop defined by the shield and arranged for engagement by the abutment to hold the locking member against rearward movement when the shield is in its set position: and resilient means acting between the locking member and the shield and arranged to urge the locking member rearwardly with respect to the shield;

whereby interaction between the cam profile and cam follower turns the locking member with respect to the support on rearward movement of the shield from its set position relative to the support, thereby rotationally shifting the locking member from the stop, and on subsequent forward movement of the shield to its locked position, the locking member further turns to allow engagement of the abutment with the shoulder of the shield, thereby preventing subsequent rearward movement of the shield from its locked position.

It will be appreciated that the device of this invention has only three components plus the resilient means which conveniently is in the form of a helical coil spring acting between the locking member and the shield. Each of the components is essentially tubular and so is relatively simple to manufacture by a plastics moulding process. This enables automated and economic manufacture on a large scale.

Preferably, the tubular support defines a bore within which a needle holder may be received, either in a frictionally-engaging pr a mechanically interlocked manner. The needle holder may be internally screw-threaded or otherwise formed for attachment to a syringe and may have a hub within which is mounted the needle, so as to project forwardly from the holder. The tubular support may include an inwardly directed lip to define a limiting forward position for a needle holder, with respect to that support.

The locking member is preferably mounted directly on an external cylindrical surface of the tubular support, whereby the locking member may both rotate and slide axially with respect to that support. That outer support may include at least one protrusion which limits the forward movement of the locking member with respect to the tubular support, whereby the locking member is given a limited degree of axial freedom, irrespective of the rotational position of the locking member with respect to the support—that is, there is lost axial motion between the locking member and the support.

In a preferred embodiment, the guide comprises one of a groove formed within the internal surface of the shield, or a slot formed through the wall of the shield. Such a groove or slot may have a forward part and a rearward part, the latter being of a greater circumferential extent than the forward part whereby said shoulder is defined at the junction between the forward and rearward parts of the groove or slot. In the case of a groove, the stop for the abutment may be provided within the groove, such that the abutment is disposed in the forward part of the groove when the abutment bears on the stop. If the guide comprises a slot through the shield wall, the stop may take the form of a further shoulder provided at the forward end of the slot, by a lateral extension to the slot. In either case, initial forward movement of the support from its set position will turn the locking member out of alignment with the stop by virtue of the interaction of the cam profile and follower while maintaining the abutment in the forward part of the groove or slot.

In an embodiment where the guide comprises a groove in the shield wall, the circumferential extent of the abutment on the locking member should be smaller than the circumferential extent of the projection on the support, such that when the abutment and projection are in the forward part of the groove, the support is restrained against rotational movement but the locking member is permitted limited rotational movement sufficient to allow the locking member to come out of alignment with the stop of the groove.

In an alternative embodiment where the guide comprises a slot through the shield wall and the stop is defined by a further shoulder as aforesaid, the circumferential extent of the abutment in the locking member may be not greater than the width of the groove in the circumferential direction, so as to be a free sliding fit therealong.

A preferred embodiment has the cam profile formed on the locking member and the cam follower provided on the support. Preferably, three such cam profiles are provided, spaced around the locking member and there are three corresponding cam followers equi-spaced around the support. Equally, the preferred embodiment has a shield which defines three guides equi-spaced around the shield and there is a like number of abutments on the locking member, though other numbers of guides and abutments could be employed.

This invention extends to a safety device of this invention as described above in combination with a medical needle provided within the tubular support and projecting forwardly therefrom. Further, this invention also extends to an injector comprising a syringe having a forwardly projecting needle (which may be removably mounted thereon) and a safety device of this invention as described above, with the support thereof mounted on the syringe.

By way of example only, one specific embodiment of safety device of this invention and for a medical needle will now be described in detail, reference being made to the accompanying drawings in which:—

Figure 1:
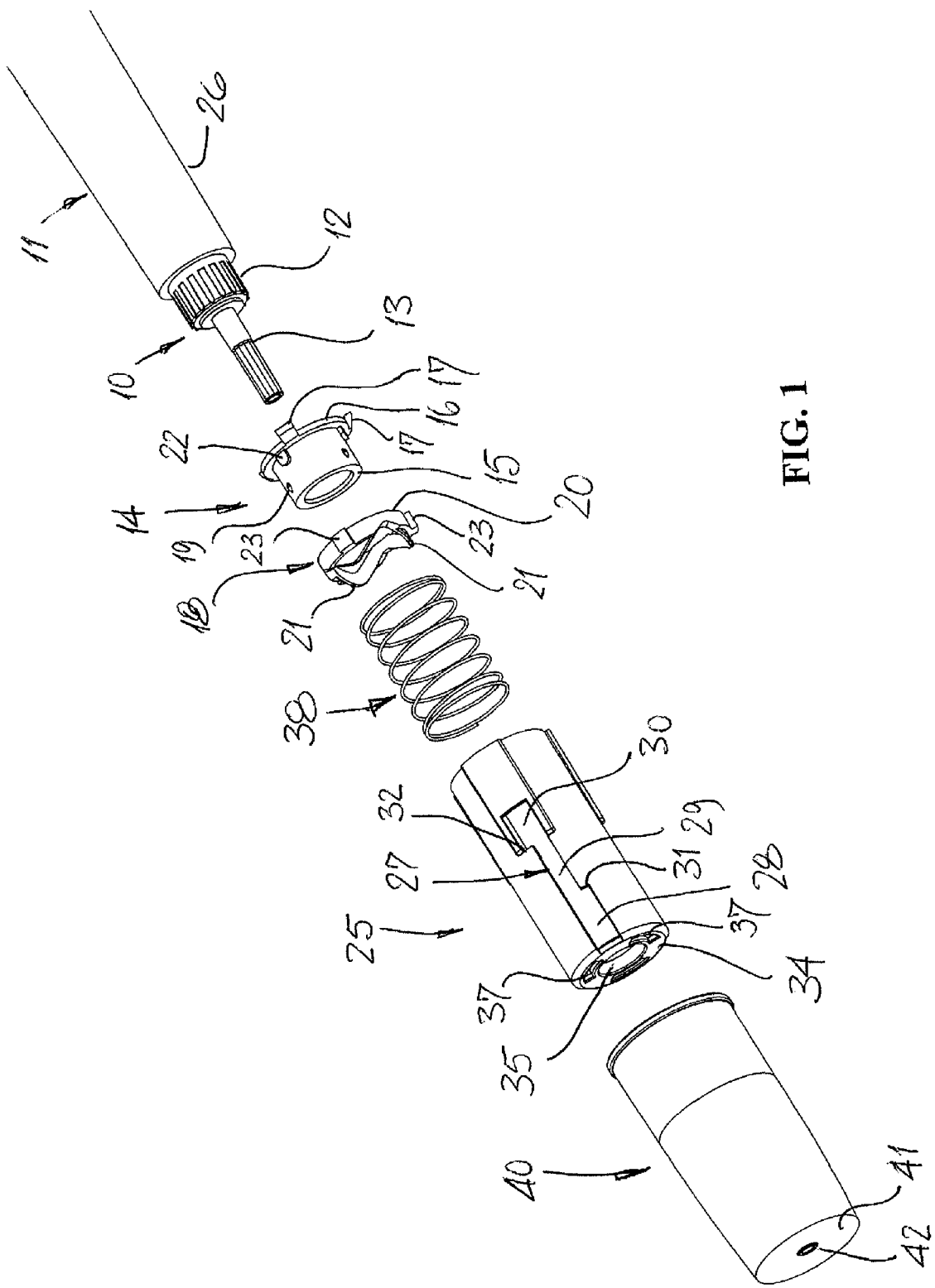
FIG. 1 is an exploded isometric view of the safety device together with a so-called pen injector shown in part and having a sheathed needle fitted to the forward end thereof.

Referring initially to FIG. 1 there are shown the components making up the safety device for use with a medical needle which, in this case, comprises a needle assembly 10 fitted to a pen injector 11. The needle assembly has an internally threaded holder 12 which is screw-fitted to an externally threaded boss at the forward end of the pen injector, the holder 12 supporting a needle which projects forwardly therefrom and is fitted with a substantially rigid sheath 13, removable for the performance of an injection. Typically, the pen injector 11 supports a cartridge of medicament having a piston at its rearward end and a bung at its forward end, which bung is penetrated by a rearward extension of the needle supported by the holder 12, as the holder is threaded to the injector. The details of the injector form no part of this invention and will not be discussed further, here.

The safety device comprises a tubular support 14 having a bore within which the holder 12 is received, when the device is fitted to the pen injector 11. As an alternative, the holder 12 could be provided within the tubular support 14 such that the safety device is fitted to the pen injector by threading the needle assembly holder 12 to the threaded boss of the injector. The forward end of the support 14 has an inwardly directed lip 15 to define a limiting position for the holder 12 within the support. At the rearward end of the support is an external flange 16 provided with three outward projections 17.

Figure 8:
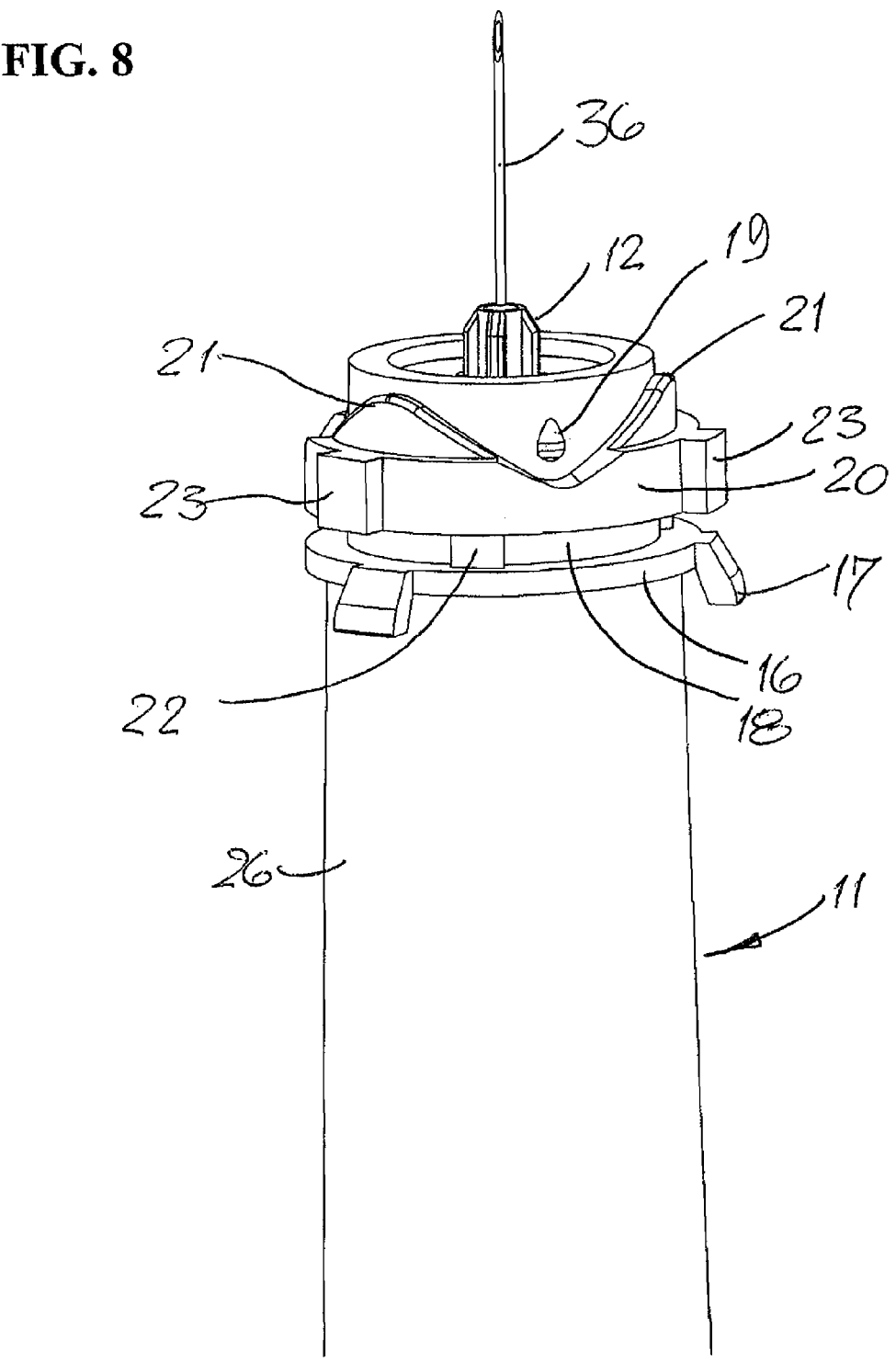
FIG. 8 is a detail view of the support and locking member fitted to a needle provided on the forward end of a pen injector.

Rotatably mounted on the external surface of the support 14 is a locking member 18, as shown in more detail in FIG. 8. That locking member is restrained on the support 14 by three protrusions 19 over which the locking member is snapped, during assembly of the device. The locking member 18 has an annular part 20 which supports three equi-spaced and essentially identical cam profiles 21, each of which co-operates with a respective cam follower 22 formed on the support 14 adjacent the external flange 16. Rotation of the locking member 18 causes the member to move axially with respect to the support, by virtue of the interaction of the cam profiles 21 with the cam followers 22. For any given rotational position of the locking member, it has a limited degree of freedom in the axial direction, defined by the protrusions 19 on the outer surface of the support 14 and the interaction between the cam profiles and followers 21,22. The protrusions 19 on the support 14 interacting with the cam profiles 21 of the locking member thus serve as limiting means for the forward movement of the locking member 18 and further, in conjunction with the cam followers 22 on the support 14, serve as limiting means for a limited degree of axial freedom of the locking member with respect to the support. Three outwardly projecting abutments 23 are provided on the external surface of the annular part 20 of the locking member for a purpose to be described below.

Figure 7:
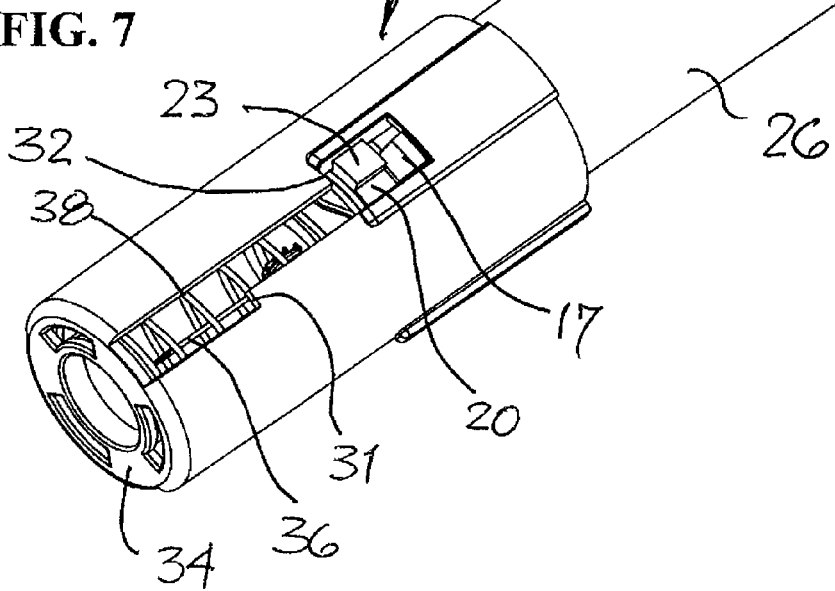
FIG. 7 shows the safety device with the shield in its locked position protecting the needle following the performance of an injection procedure.

The safety device further comprises a shield 25 having a bore which is selected for use with a particular design of injector, so as to be a sliding fit over the barrel 26 thereof. The wall of the shield has three equi-spaced axially-extending slots 27 formed therethrough, from the forward end of the shield back towards the rear end thereof. Each slot has a forward part 28, a central part 29 and a rearward part 30, the circumferential extent of the forward and rearward parts being greater than that of the central part, whereby a first shoulder 31 is defined between the forward and central parts and a second shoulder 32 is defined between the central and rearward parts. The external flange 16 of the support 14 is a free sliding fit within the bore of the shield 25, with the projections 17 received in the slots 27. When the projections are in the central parts 29 of the slots 27, the support is held against rotational movement with respect to the shield, but when the projections are in the rearward parts 30, the support may rotate through a limited extent defined by the greater circumferential extent of the rearward parts of the slots (FIG. 7). As will be described below, the arrangement is such that the tubular support 14 cannot move sufficiently forwardly with respect to the shield for the projections 17 to leave the central parts 29 of the slots 27.

Figure 5:
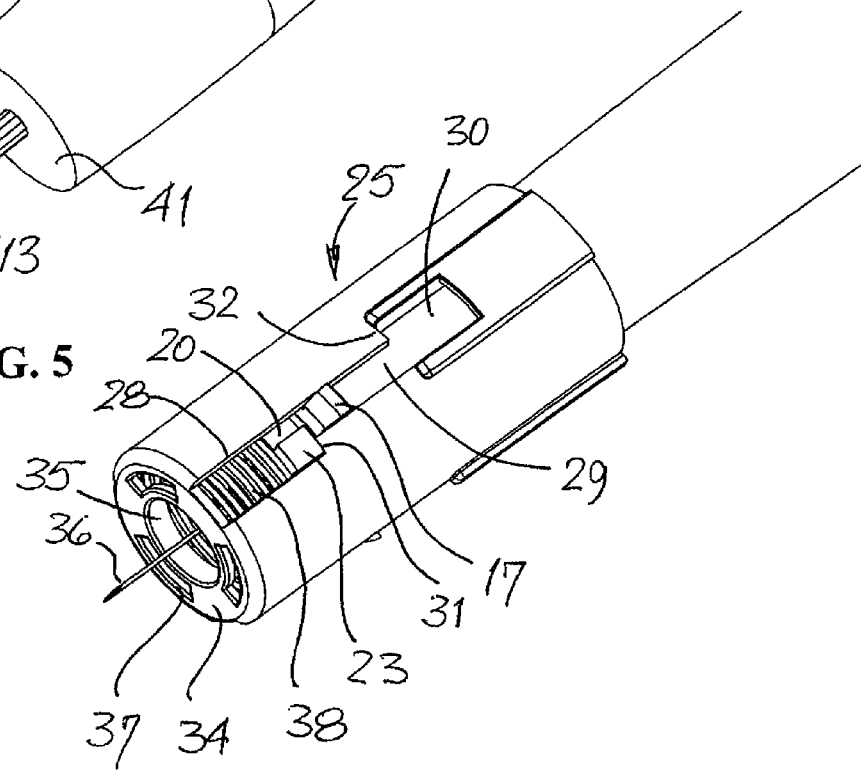
FIG. 5 shows the safety device in its initial, set position.
Figure 6:
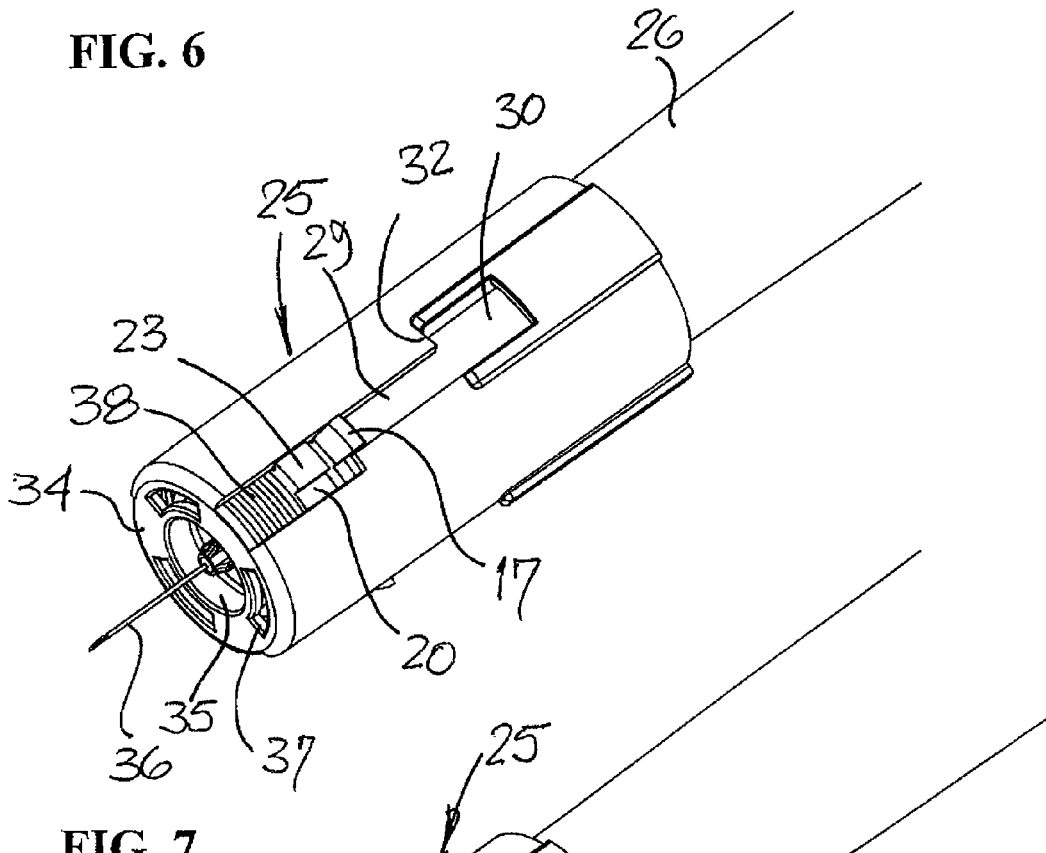
FIG. 6 shows the safety device with the shield fully withdrawn from the needle, during the performance of an injection procedure.
Figure 9:
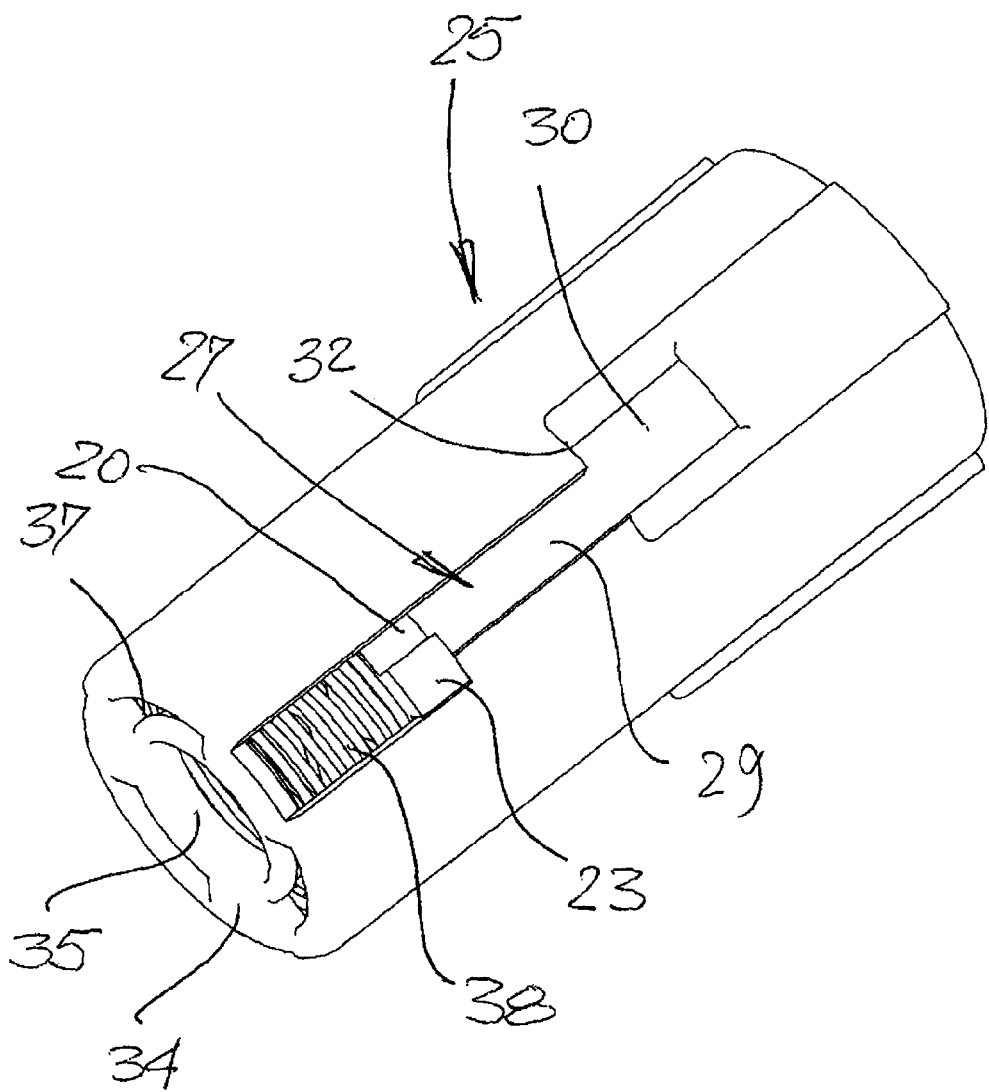
FIG. 9 is a detail view on an enlarged scale of the tubular shield, locking member and spring but with the other components removed for clarity, when the locking member is in its initial, set position.

The abutments 23 of the locking member 18 have substantially the same circumferential extent as the projections 17 and are also received within the slots 27. Thus, the abutments 23 may locate in the forward parts 28 of the slots 27 as shown in FIGS. 5, 6 and 9 and also in the rearward part 30 of the slots as shown in FIG. 7. When located in the forward parts 28, each abutment may engage behind the respective first shoulder 31 (FIG. 5) by rotation of the locking member 18 in one sense with respect to the sheath 13 and support 14. When located in the rearward parts 30, each abutment may engage behind the respective second shoulder 32 (FIG. 7) by rotation of the locking member 18 in the opposed sense with respect to the sheath 13 and support 14.

At its forward end, the shield 25 has an inwardly projecting flange 34 with a central hold 35 through which the needle 36 of the needle assembly 10 may, in use, project. The flange 34 has three slots 37 formed therein, to permit the insertion of the prongs of an assembly tool (not shown) for facilitating alignment of the components described above, during the manufacture of the device. A helical compression spring 38, serving as a resilient means for urging the locking member rearwardly with respect to the shield 25, is disposed between the flange 34 and the annular part 20 of the locking member 18. The support 14 is thus also urged rearwardly by virtue of the interaction between the cam profiles 21 and cam followers 22 on the locking member and support respectively, but subject to the limited axial freedom between those components.

In the initial, set position of the device, the abutments 23 of the locking member 18 are located in the forward parts 28 of the slots 27, engaged behind the respective first shoulders 31, so holding both the locking member 18 and support 14 against rearward movement with respect to the shield 25. The projections 17 of the tubular support 14 are disposed in the central parts 29 of the slots 27, so holding the support 14 against rotation with respect to the shield. Relative rotation of the locking member with respect to the shield allows the abutments 23 to come free of the first shoulders 31 whereafter the locking member and support may move rearwardly with respect to the shield. Once those components have moved rearwardly sufficiently to bring the abutments 23 rearwardly of the second shoulders 32, further rotation of the locking member with respect to the shield will bring those abutments behind the second shoulders and so prevent subsequent forward movement of the locking member and support, with respect to the shield.

Figure 2:
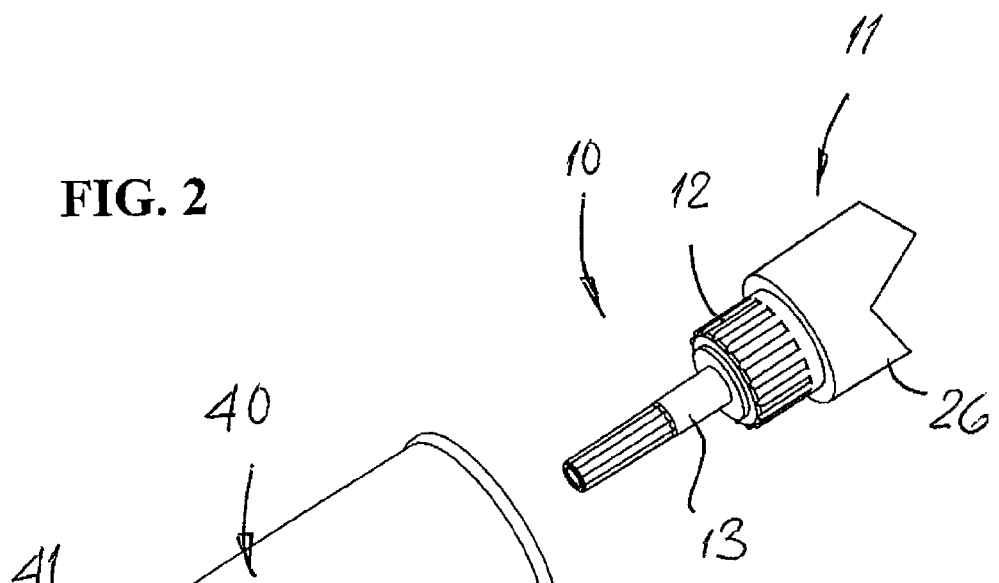
FIG. 2 is an isometric view of the safety device disposed within its container and being offered to a pen injector having a sheathed needle fitted thereto.
Figure 3:
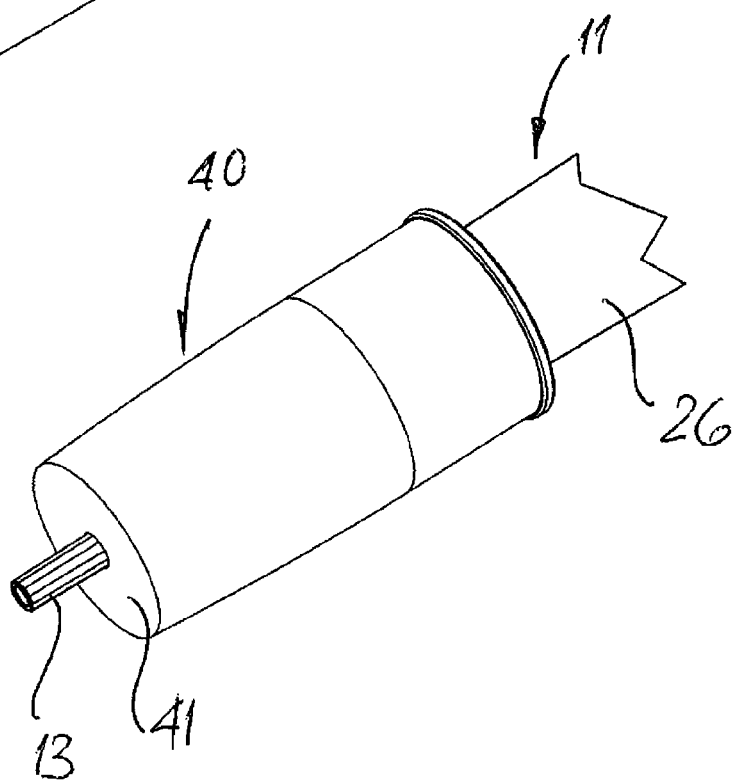
FIG. 3 is an isometric view of the safety device having the sheathed needle fully inserted therein.
Figure 4:
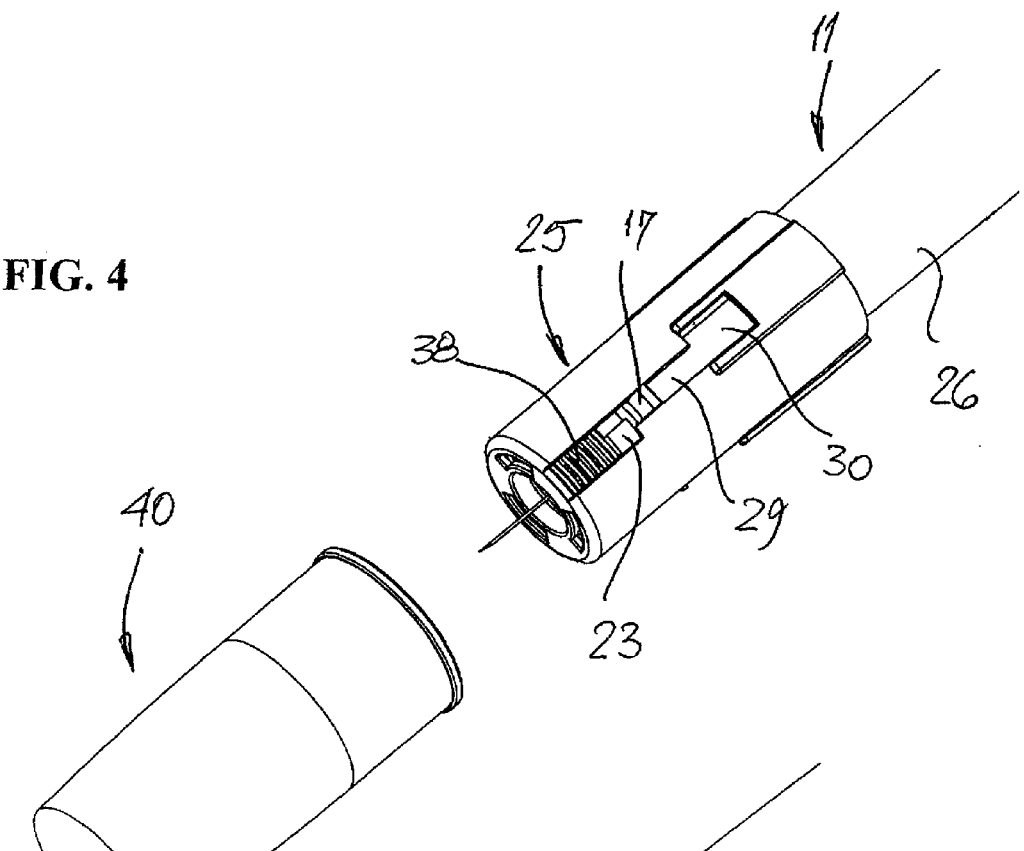
FIG. 4 is an isometric view of the pen injector removed from the container of the safety device, with the needle exposed ready for performing an injection procedure.

FIGS. 2, 3 and 4 show the initial stages of the use of the device, prior to the performance of an injection. The assembled safety device with the abutments 23 engaged behind the first shoulders 31 of the sheath and held there by the force of spring 38 is disposed within a container 40 having a front wall 41 provided with a central hole 42 which is a friction fit over the sheath 13 of the needle assembly 10. The rear end of the container 40 is open, but may be closed by a strippable seal (not shown) and which is removed immediately prior to use of the device. The injector 11 is prepared by fitting a sheathed needle assembly thereto, in an entirely conventional manner. The injector and needle assembly are then offered to the safety device (FIG. 2) and pushed fully into the container 40 so that the sheath 13 projects through the central hole 42 in the front wall 41 of the container 40; the holder 12 of the needle assembly 10 is then fully received within the tubular support 14, engaged with the lip 15 thereof.

The injector 11 is then pulled away from the container 40. This leaves the sheath 13 frictionally engaged with the front wall 41 of the container 40, de-sheathing the needle 36 so as to be ready for use. A significant length of the needle 36 is exposed beyond the flange 34 at the forward end of the shield 25, whereby the user may observe the injection site and use the pen injector in essentially the same manner as if the safety device were not fitted thereto. However, on performing the injection by pushing the pen injector into the injection site, the needle 36, support 14 and locking member 18 all move forwardly with respect to the shield 25—that is, the shield moves rearwardly with respect to the injector 11. During the initial stage of this forward movement of the injector, the pressure on the support 14 is transferred to the locking member 18 through the interaction of the cam followers 22 bearing on the cam profiles 21, along with the rearward force of the spring 38 also acting on the locking member. This serves to rotate the locking member 18 to move the abutments 23 out of alignment with the first shoulders 31 and into alignment with the central part 29 of the respective slot 27. The fully forward position (FIG. 6) is defined by the turns of the spring 38 binding: in this position, the projections 17 of the support 14 are still disposed within the central parts 29 of the slots 27.

On moving the injector 11 away from the injection site, the support 14 and locking member 18 move rearwardly with respect to the shield 25 under the action of spring 38. The support 14 moves rearwardly until the abutments 23 reach the rearward ends of the slots 27 (FIG. 7) but there is still a rearward spring force acting on the locking member 18. This force in conjunction with the interengaged cam profiles 21 and followers 22, serves to rotate the locking member 18 yet further, to bring the abutments 23 thereof behind the second shoulders 32 of the slots 27. If now rearward pressure is applied to the shield 25, the support 14 and locking member 18 cannot move forwardly within the shield, by virtue of the interengagement of the abutments 23 with the second shoulders 32. The shield is thus effectively locked in a protecting position where the needle 36 is wholly covered by the shield 25.

Once locked as described above, the entire device may be rotated to unscrew the holder 12 of the needle assembly 10 from the injector 11, thus releasing the needle 36 which may remain protected within the device. The combination of the device and needle may then be disposed of in a safe manner, for example by depositing that combination within a sharps container. As an alternative, the entire device may be reinserted into the container 40 and the injector then unscrewed from the needle assembly, so leaving the device within the container ready for disposal.

The invention claimed is:

1. A safety device for a medical needle having a mount end and a sharp tip, which device comprises:
    a tubular support directly or indirectly associated with the needle mount end;
    a tubular protective shield disposed co-axially on the support for sliding movement with respect thereto from a set position where a part of the length of the needle back from its tip is exposed, to a fully retracted position and then to a locked position where the shield covers the needle to afford protection thereto, the shield and support being restrained against significant relative rotational movement;
    a locking member rotationally mounted on the support within the shield, there being a cam profile on one of the locking member and support and a cam follower on the other of the locking member and support whereby forward axial movement of the support with respect to the locking member causes the locking member to rotate relative to the support;
    a guide extending generally axially of the shield and defining a shoulder towards the rearward end thereof;
    an abutment on the locking member engageable with the guide and receivable behind said shoulder when the shield is in its locked position;
    resilient means for urging the locking member rearwardly, said resilient means acting between the locking member and the shield thereby to urge the locking member rearwardly with respect to the shield; and
    a stop defined by the shield and positioned for engagement by the abutment to hold the locking member against rearward movement under the action of said resilient means when the shield is in its set position;
    whereby rearward movement of the shield from its set position relative to the support causes interaction between the cam profile and cam follower to turn the locking member with respect to the support thereby rotationally shifting the locking member from said stop, and on subsequent forward movement of the shield to its locked position under the action of said resilient means, the interaction between the cam profile and cam follower causes the locking member to turn further to allow engagement of the abutment with the shoulder of the shield, thereby preventing subsequent rearward movement of the shield from its locked position.

2. A safety device as claimed in claim 1, wherein the tubular support defines a bore for receiving a needle holder supporting the needle, thereby to permit the mounting of the device on the needle.

3. A safety device as claimed in claim 1, wherein the tubular support defines a cylindrical outer surface on which the locking member is rotationally mounted.

4. A safety device as claimed in claim 3, wherein the outer surface of the tubular support includes limiting means for limiting the forward movement of the locking member with respect to the tubular support.

5. A safety device as claimed in claim 4, wherein said limiting means co-acts with the cam profile to give the locking member a limited degree of axial freedom with respect to the support.

6. A safety device as claimed in claim 1, wherein the guide comprises one of a groove formed in the shield.

7. A safety device as claimed in claim 6, wherein the guide has a central part and a rearward part of a greater circumferential extent than the central part, and the shoulder is defined at the junction between the central and rearward parts.

8. A safety device as claimed in claim 7, wherein the guide has a forward part and said stop is formed between the central and forward parts.

9. A safety device as claimed in claim 8 wherein the forward part is of a greater circumferential extent than the central part and the stop is defined by the junction between the central and forward parts.

10. A safety device as claimed in claim 6, wherein the tubular support includes an outwardly directed projection which is received by the guide, thereby to restrain rotational movement between the support and the shield.

11. A safety device as claimed in claim 1, wherein the cam profile is formed on the locking member and the cam follower is provided on the support.

12. A safety device as claimed in claim 11, wherein the locking member has three essentially identical cam profiles disposed around the periphery thereof, and the support has three equi-spaced cam followers associated one with each cam profile respectively.

13. A safety device as claimed in claim 1, wherein there are three guides formed within the shield and each having associated therewith a respective shoulder and stop.

14. A safety device as claimed in claim 1, wherein the resilient means comprises a helical compression spring.

15. A safety device as claimed in claim 14, wherein the forward end of the shield has an inwardly directed flange and said spring bears against the flange.

16. A safety device as claimed in claim 14, wherein the locking member has an annular part and a cam profile part, the spring acting on the annular part of the locking member to urge the locking member rearwardly with respect to the shield.

17. A safety device as claimed in claim 1, wherein there is provided a container for the shield, said container being open at one end and having a wall at its other end, said wall being provided with a central hole for receiving a sheath of a needle.

18. A safety device as claimed in claim 1 in combination with a medical needle provided within the tubular support and projecting forwardly therefrom.

19. An injector comprising a syringe having a forwardly projecting needle and a safety device as claimed in claim 1, with the support thereof mounted on the syringe.

* * * * *